(12) United States Patent
Fawcett

(10) Patent No.: US 7,858,365 B2
(45) Date of Patent: *Dec. 28, 2010

(54) SAMPLE BLOCK APPARATUS AND METHOD FOR MAINTAINING A MICROCARD ON A SAMPLE BLOCK

(75) Inventor: Adrian Fawcett, Pleasanton, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/249,007

(22) Filed: Oct. 10, 2008

(65) Prior Publication Data

US 2009/0029454 A1 Jan. 29, 2009

Related U.S. Application Data

(63) Continuation of application No. 10/207,263, filed on Jul. 30, 2002, now Pat. No. 7,452,712.

(51) Int. Cl.
C12M 1/34 (2006.01)
C12M 1/38 (2006.01)

(52) U.S. Cl. .............. 435/288.4; 435/287.2; 435/288.7; 435/303.1; 435/809; 435/287.3

(58) Field of Classification Search .............. 435/287.3, 435/288.4, 288.7, 303.1, 809
See application file for complete search history.

(56) References Cited

U.S. PATENT DOCUMENTS

| | | | |
|---|---|---|---|
| 3,848,962 A | 11/1974 | Nelson | |
| 4,097,116 A | 6/1978 | Kuroha | |
| 4,186,305 A | 1/1980 | Taoka et al. | |
| 4,285,568 A | 8/1981 | Elgart | |
| 4,313,679 A | 2/1982 | Wolff et al. | |

(Continued)

FOREIGN PATENT DOCUMENTS

JP 7-508928 10/1995

(Continued)

OTHER PUBLICATIONS 03795576.2, "International Search Report received for PCT Application No. PCT/US03/023750 mailed on Oct. 18, 2004".

(Continued)

Primary Examiner—William H Beisner

(57) ABSTRACT

A thermal cycling device for thermally cycling samples of biological material contained in a microcard having a top and bottom surface. The thermal cycling device can include a sample block having an upper surface configured for engaging the bottom surface of a microcard, a vacuum device, and a temperature control system operatively connected with the sample block. The upper surface of the sample block may include a plurality of channels, the channels defining spaces between the sample block and the bottom surface of a microcard that may be positioned thereon. The vacuum device may be in fluid communication with the sample block for drawing gas out of the spaces defined by the channels in the sample block. The vacuum device may be configured for substantially maintaining a vacuum between the sample block and microcard so that a retention force is imparted on the microcard to urge the microcard toward the sample block. Methods of maintaining a microcard on a sample block of a thermal cycling device are also provided.

11 Claims, 9 Drawing Sheets

U.S. PATENT DOCUMENTS

| | | |
|---|---|---|
| 4,526,445 A | 7/1985 | Wogoman |
| 4,554,839 A | 11/1985 | Hewett et al. |
| 4,577,141 A | 3/1986 | Saiki et al. |
| 4,679,615 A | 7/1987 | Livne et al. |
| 4,822,741 A | 4/1989 | Banes |
| 4,865,461 A | 9/1989 | Taylor et al. |
| 4,952,518 A | 8/1990 | Johnson et al. |
| 5,066,377 A | 11/1991 | Rosenbaum et al. |
| 5,224,778 A | 7/1993 | Grossman et al. |
| 5,240,857 A | 8/1993 | Lahetkangas |
| 5,255,976 A | 10/1993 | Connelly |
| 5,281,794 A | 1/1994 | Uehara |
| 5,320,808 A | 6/1994 | Holen et al. |
| 5,333,675 A | 8/1994 | Mullis et al. |
| 5,342,581 A | 8/1994 | Sanadi |
| 5,343,012 A | 8/1994 | Hardy et al. |
| 5,368,645 A | 11/1994 | Bok |
| 5,397,919 A | 3/1995 | Tata et al. |
| 5,416,329 A | 5/1995 | Sonne et al. |
| 5,446,263 A * | 8/1995 | Eigen et al. .................. 219/521 |
| 5,475,610 A | 12/1995 | Atwood |
| 5,489,532 A | 2/1996 | Charm et al. |
| 5,508,197 A | 4/1996 | Hansen et al. |
| 5,525,300 A | 6/1996 | Danssaert et al. |
| 5,534,073 A | 7/1996 | Kinoshita et al. |
| 5,587,128 A | 12/1996 | Wilding et al. |
| 5,587,321 A | 12/1996 | Smith et al. |
| 5,604,130 A * | 2/1997 | Warner et al. ............. 435/286.7 |
| 5,616,301 A | 4/1997 | Moser et al. |
| 5,618,759 A * | 4/1997 | Boysel ........................ 438/464 |
| 5,656,493 A | 8/1997 | Mullis et al. |
| 5,660,758 A | 8/1997 | McCullough |
| 5,665,599 A | 9/1997 | Minuth |
| 5,667,870 A | 9/1997 | McCullough et al. |
| 5,703,342 A | 12/1997 | Hoffmann et al. |
| 5,720,923 A | 2/1998 | Haff et al. |
| 5,736,106 A | 4/1998 | Ishiguro et al. |
| 5,738,165 A * | 4/1998 | Imai ......................... 165/80.2 |
| 5,741,463 A | 4/1998 | Sanadi |
| 5,774,335 A | 6/1998 | Pare et al. |
| 5,779,981 A | 7/1998 | Danssaert et al. |
| 5,784,257 A | 7/1998 | Tata |
| 5,795,547 A | 8/1998 | Moser et al. |
| 5,802,856 A | 9/1998 | Schaper et al. |
| 5,819,842 A | 10/1998 | Potter et al. |
| 5,825,622 A | 10/1998 | Rife et al. |
| 5,837,546 A | 11/1998 | Allen et al. |
| 5,846,595 A | 12/1998 | Sun et al. |
| 5,866,342 A | 2/1999 | Antonenko et al. |
| 5,882,465 A | 3/1999 | McReynolds |
| 5,897,842 A | 4/1999 | Dunn et al. |
| 5,928,907 A | 7/1999 | Woudenberg et al. |
| 5,939,312 A | 8/1999 | Baier et al. |
| 5,942,312 A | 8/1999 | Venkataraman et al. |
| 5,945,736 A | 8/1999 | Rife et al. |
| 5,959,098 A | 9/1999 | Goldberg |
| 5,981,956 A | 11/1999 | Stern |
| 5,983,644 A | 11/1999 | Bolandi et al. |
| 5,985,214 A | 11/1999 | Stylli |
| 5,989,760 A | 11/1999 | Mangat et al. |
| 6,001,309 A | 12/1999 | Gamble et al. |
| 6,014,315 A | 1/2000 | McCullough |
| 6,015,674 A | 1/2000 | Woudenberg et al. |
| 6,018,616 A | 1/2000 | Schaper |
| 6,020,187 A | 2/2000 | Tam |
| 6,021,045 A | 2/2000 | Johnson |
| 6,033,880 A | 3/2000 | Haff et al. |
| 6,043,880 A | 3/2000 | Andrews et al. |
| 6,054,263 A | 4/2000 | Danssaert et al. |
| 6,075,699 A | 6/2000 | Rife |
| 6,082,797 A | 7/2000 | Antonette |
| 6,093,961 A | 7/2000 | McCullough |
| 6,099,230 A | 8/2000 | Hitch |
| 6,106,784 A | 8/2000 | Lund et al. |
| 6,124,138 A | 9/2000 | Woudenberg et al. |
| 6,129,546 A | 10/2000 | Sada |
| 6,132,996 A | 10/2000 | Hunicke-Smith |
| 6,140,044 A | 10/2000 | Besemer et al. |
| 6,141,096 A | 10/2000 | Stern et al. |
| 6,153,426 A | 11/2000 | Heimberg |
| 6,197,572 B1 | 3/2001 | Schneebeli |
| 6,201,697 B1 | 3/2001 | McCullough |
| 6,210,958 B1 | 4/2001 | Brust et al. |
| 6,214,263 B1 | 4/2001 | McCullough |
| 6,220,451 B1 | 4/2001 | Hoffmann |
| 6,228,659 B1 | 5/2001 | Kowallis et al. |
| 6,237,223 B1 | 5/2001 | McCullough |
| 6,252,774 B1 | 6/2001 | Rife |
| 6,253,807 B1 | 7/2001 | Jones |
| 6,272,939 B1 | 8/2001 | Frye et al. |
| 6,293,331 B1 | 9/2001 | Wang |
| 6,304,451 B1 | 10/2001 | Rife |
| 6,323,035 B1 | 11/2001 | Kedar et al. |
| 6,325,114 B1 | 12/2001 | Bevirt et al. |
| 6,337,435 B1 | 1/2002 | Chu et al. |
| 6,343,012 B1 | 1/2002 | Rife |
| 6,372,185 B1 | 4/2002 | Shumate et al. |
| 6,372,486 B1 | 4/2002 | Fripp |
| 6,385,047 B1 | 5/2002 | McCullough et al. |
| 6,394,797 B1 * | 5/2002 | Sugaya et al. ............... 432/253 |
| 6,399,952 B1 * | 6/2002 | Maher et al. ............. 250/458.1 |
| 6,410,231 B1 | 6/2002 | Arnold et al. |
| 6,416,719 B1 | 7/2002 | Fawcett et al. |
| 6,420,180 B1 | 7/2002 | Bass |
| 6,426,215 B1 | 7/2002 | Sandell |
| 6,447,723 B1 | 9/2002 | Schermer |
| 6,468,800 B1 | 10/2002 | Stylli et al. |
| 6,479,301 B1 | 11/2002 | Balch et al. |
| 6,482,588 B1 | 11/2002 | Van Doorn et al. |
| 6,485,903 B1 | 11/2002 | Mayrand |
| 6,485,944 B1 | 11/2002 | Church et al. |
| 6,506,611 B2 | 1/2003 | Bienert et al. |
| 6,514,750 B2 | 2/2003 | Bordenkircher et al. |
| 6,544,477 B1 | 4/2003 | Blumenfeld et al. |
| 6,552,784 B1 | 4/2003 | Dietz et al. |
| 6,558,623 B1 | 5/2003 | Ganz et al. |
| 6,558,947 B1 | 5/2003 | Lund et al. |
| 6,563,581 B1 | 5/2003 | Oldham et al. |
| 6,599,693 B1 | 7/2003 | Webb |
| 6,610,470 B2 | 8/2003 | Blumenfeld et al. |
| 6,627,446 B1 | 9/2003 | Roach et al. |
| 6,660,233 B1 | 12/2003 | Coassin et al. |
| 6,672,344 B1 | 1/2004 | Stokes et al. |
| 6,677,151 B2 | 1/2004 | Sandell |
| 6,678,577 B1 | 1/2004 | Stylli et al. |
| 6,685,884 B2 | 2/2004 | Stylli et al. |
| 6,703,247 B1 | 3/2004 | Chu |
| 6,730,883 B2 | 5/2004 | Brown et al. |
| 6,733,729 B2 | 5/2004 | Blumenfeld et al. |
| 6,744,502 B2 | 6/2004 | Hoff et al. |
| 6,752,182 B2 | 6/2004 | Atkinson et al. |
| 6,762,049 B2 | 7/2004 | Zou et al. |
| 6,764,818 B2 | 7/2004 | Lafferty |
| 6,821,375 B2 * | 11/2004 | Ulrich ........................ 156/285 |
| 6,852,986 B1 | 2/2005 | Lee et al. |
| 2001/0049134 A1 | 12/2001 | Lee et al. |
| 2002/0001848 A1 | 1/2002 | Bedingham et al. |
| 2002/0006619 A1 | 1/2002 | Cohen et al. |
| 2002/0015995 A1 | 2/2002 | Blumenfeld et al. |
| 2002/0047003 A1 | 4/2002 | Bedingham et al. |
| 2002/0048533 A1 | 4/2002 | Harms et al. |
| 2002/0064885 A1 | 5/2002 | Bedingham et al. |
| 2002/0098593 A1 | 7/2002 | Neilson et al. |
| 2002/0119077 A1 | 8/2002 | Shumate et al. |

| | | | |
|---|---|---|---|
| 2002/0127660 A1 | 9/2002 | Danssaert et al. | |
| 2002/0142349 A1 | 10/2002 | Tennstedt et al. | |
| 2002/0173048 A1 | 11/2002 | Nakazawa et al. | |
| 2002/0176803 A1 | 11/2002 | Hamel et al. | |
| 2002/0182117 A1 | 12/2002 | Coassin et al. | |
| 2003/0008286 A1 | 1/2003 | Zou et al. | |
| 2003/0017085 A1 | 1/2003 | Kercso et al. | |
| 2003/0032198 A1 | 2/2003 | Lugmair et al. | |
| 2003/0092064 A1 | 5/2003 | Reader | |
| 2003/0096427 A1 | 5/2003 | Hall | |
| 2003/0124735 A1 | 7/2003 | Nanthakumar et al. | |
| 2003/0138829 A1 | 7/2003 | Unger et al. | |
| 2003/0157563 A1 | 8/2003 | Danssaert et al. | |
| 2003/0160957 A1 | 8/2003 | Oldham et al. | |
| 2003/0161761 A1 | 8/2003 | Williams et al. | |
| 2003/0170883 A1 | 9/2003 | Martin et al. | |
| 2003/0198575 A1 | 10/2003 | Noda et al. | |
| 2003/0215360 A1 | 11/2003 | Ruddock | |
| 2003/0215956 A1 | 11/2003 | Reed | |
| 2004/0018635 A1 | 1/2004 | Peck et al. | |
| 2004/0062686 A1 | 4/2004 | Ganz et al. | |
| 2004/0096984 A1 | 5/2004 | Elverd et al. | |
| 2004/0110275 A1 | 6/2004 | Sandell | |
| 2004/0126283 A1 | 7/2004 | Backes et al. | |
| 2004/0136868 A1 | 7/2004 | Bevirt et al. | |
| 2004/0191896 A1 | 9/2004 | Miao et al. | |
| 2004/0202577 A1 | 10/2004 | McNeil et al. | |

FOREIGN PATENT DOCUMENTS

| | | |
|---|---|---|
| JP | 9-511407 | 11/1997 |
| JP | 10-284360 | 10/1998 |
| JP | 2000-508528 | 7/2000 |
| WO | WO-95/11262 | 4/1995 |
| WO | WO-95/30139 | 11/1995 |
| WO | WO-96/33010 | 10/1996 |
| WO | WO-97/36681 | 10/1997 |
| WO | WO-98/47003 | 10/1998 |
| WO | WO-99/60381 | 11/1999 |
| WO | WO-00/25922 | 5/2000 |
| WO | WO-01/28684 | 4/2001 |
| WO | WO 0128684 A2 * | 4/2001 |
| WO | WO-01/35079 | 5/2001 |
| WO | WO-02/01180 | 1/2002 |
| WO | WO-02/01181 | 1/2002 |
| WO | WO-02/16546 | 2/2002 |

OTHER PUBLICATIONS 03795576.2, "European Search Report mailed Jun. 25, 2009".
03795576.2, "EP Office action mailed on Sep. 25, 2009".
U.S. Appl. No. 10/207,263, "Notice of Allowance mailed on Jul. 10, 2008".
U.S. Appl. No. 10/207,263, "Office Action mailed Jan. 2, 2008".
U.S. Appl. No. 10/207,263, "Office Action mailed Jan. 27, 2006".
U.S. Appl. No. 10/207,263, "Office Action mailed Mar. 17, 2005".
U.S. Appl. No. 10/207,263, "Office Action mailed Apr. 6, 2007".
U.S. Appl. No. 10/207,263, "Office Action mailed Oct. 1, 2004".
U.S. Appl. No. 10/207,263, "Office Action mailed Oct. 19, 2006".
U.S. Appl. No. 10/207,263, "Response to Jan. 27, 2006 Office Action", Filed Jun. 19, 2006.
U.S. Appl. No. 10/207,263, "Response to Jan. 2, 2008 Office Action", Filed Mar. 31, 2008.
U.S. Appl. No. 10/207,263, "Response to Jan. 267, 2006 Office Action", Filed Jul. 24, 2006.
U.S. Appl. No. 10/207,263, "Response to Mar. 17, 2005 Office Action", Filed Jun. 17, 2005.
U.S. Appl. No. 10/207,263, "Response to Mar. 17, 2005 Office Action", Filed Jul. 27, 2005.
U.S. Appl. No. 10/207,263, "Response to Apr. 6, 2007 Office Action", Filed Oct. 3, 2007.
U.S. Appl. No. 10/207,263, "Response to Oct. 1, 2004 Office Action", Filed Dec. 30, 2004.
U.S. Appl. No. 10/207,263, "Response to Oct. 19, 2006 Office Action", Filed Jan. 19, 2007.
2003296707,"AU Office Action mailed May 25, 2006".
2004-535990, "JP Office Action mailed Nov. 7, 2007".
PCT/US03/23750, "International Search Report received for PCT Application No. PCT/US03/23750 mailed on Oct. 18, 2004".

* cited by examiner

SAMPLE BLOCK APPARATUS AND METHOD FOR MAINTAINING A MICROCARD ON A SAMPLE BLOCK

CROSS-REFERENCE TO RELATED APPLICATIONS

This application is a continuation of U.S. patent application Ser. No. 10/207,263 filed on Jul. 30, 2002 now U.S. Pat. No. 7,452,712. The entire disclosure of the above application is incorporated herein by reference.

FIELD

The present teachings relate generally to sample block apparatus suitable for use in a thermal cycling device, and methods of maintaining a microcard on a sample block of a thermal cycling device. More particularly, the present teachings further relate, in various aspects, to sample block apparatus utilizing a vacuum to maintain a microcard on a sample block during a nucleic acid amplification process such as polymerase chain reaction (PCR).

BACKGROUND

Biological testing has become an important tool in detecting and monitoring diseases. In the biological testing field, thermal cycling is used to amplify nucleic acids by, for example, performing PCR and other reactions. PCR in particular has become a valuable research tool with applications such as cloning, analysis of genetic expression, DNA sequencing, and drug discovery.

Recent developments in the field have spurred growth in the number of tests that are performed. One method for increasing the information obtainable through such biological testing is to provide real-time detection capability during thermal cycling. During real-time detection the characteristics of samples of biological materials can be detected while the sample well tray remains positioned in the thermal cycling device. A method for increasing throughput is to place a large number of samples on a single microcard. In this manner, more tests may be performed in a given period of time. Moreover, it is possible to reduce costs by running at low reaction volumes of biological materials. It may also be desirable for there to be substantial temperature uniformity between the plurality of samples on a single microcard.

SUMMARY

Various aspects generally relate to, among other things, a thermal cycling device for thermal cycling samples of biological material contained in a microcard.

Various aspects provide a thermal cycling device for thermally cycling samples of biological material contained in a microcard having a top and bottom surface. The thermal cycling device can comprise a sample block having an upper surface configured for engaging the bottom surface of a microcard, a vacuum device, and a temperature control system operatively connected with the sample block. The upper surface of the sample block may include a plurality of channels, the channels defining spaces between the sample block and the bottom surface of a microcard that may be positioned thereon. The vacuum device may be in fluid communication with the sample block for drawing gas out of the spaces defined by the channels in the sample block. The vacuum device may be configured for substantially maintaining a vacuum between the sample block and microcard so that a retention force is imparted on the microcard to urge the microcard toward the sample block. The temperature control system may be configured for cycling the sample block through a sequence of times and temperatures comprising at least a first temperature maintained for a first period of time and a second temperature maintained for a second period of time, with the second temperature being higher than the first temperature, and the cycling comprising at least two repetitions of said sequence of time and temperatures.

Various other aspects comprise a sample block apparatus for a thermal cycler configured for use with a microcard containing a plurality of samples of biological material. The sample block apparatus can comprise a sample block, a vacuum source, and a temperature control system operatively connected with the sample block to cycle the sample block according to a user-defined profile. The sample block can comprise an upper surface configured for resting a microcard thereon, the upper surface including surface irregularities for defining spaces between the surface irregularities and a microcard that may be positioned thereon. The vacuum source may be in fluid communication with the space between the surface irregularity and the microcard positioned thereon. The vacuum source may be configured to create a substantial vacuum in the spaces thereby imparting a force on the microcard to retain the microcard on the sample block upper surface.

Further various aspects comprise a microcard retaining apparatus for a thermal cycler of biological materials. The microcard retaining apparatus can comprise a sample block having a an upper surface and a vacuum port. The sample block upper surface may be substantially flat and configured to engage a bottom surface of a microcard that may be positioned thereon. The upper surface of the sample block may further comprise a plurality of recesses. The vacuum port in the sample block may be in fluid communication with the plurality of recesses to assist in imparting a vacuum in the recesses to cause the microcard to press downward against the upper surface of the sample block. The vacuum port may be configured for attachment to a vacuum source.

Various aspects also comprise a method of maintaining a microcard on a sample block of a thermal cycling device. The method can include the steps of providing a sample block with a plurality of channels on an upper surface thereof. The method may further include the step of providing a space for a microcard containing at least one sample of biological material above the upper surface of the sample block so that a bottom surface of the microcard may contact the upper surface of the sample block. A vacuum may be imparted on the spaces defined by the channels on the upper surface of the sample block and the bottom surface of the microcard positioned adjacent the upper surface of the sample block, the vacuum creating a force to urge the microcard against the upper surface of the sample block. The microcard may then be thermally cycled through a sequence of times and temperatures comprising at least a first temperature maintained for a first period of time and a second temperature maintained for a second period of time, with said second temperature being higher than said first temperature. Optionally, simultaneously with the step of thermally cycling the microcard, the optical characteristics of the at least one sample of biological material may be detected.

Further various aspects comprise an apparatus for thermally cycling samples of biological material contained in a microcard. The apparatus can comprise a sample block configured to assist in heating and cooling a microcard during thermal cycling, means for urging a microcard against a top surface of a sample block of a thermal cycling device using a vacuum, and means for imposing a substantial vacuum in a space between the sample block and the microcard.

Still further various aspects comprise a thermal cycling apparatus. The thermal cycling apparatus can comprise a base, with said base defining a void therein, a vacuum port disposed for fluid communication with the void, support features disposed adjacent the void on the base, and a temperature control system. The support features include uppermost surface regions defining a common plane. The temperature control system may be configured for cycling at least one of the base and the support features through a sequence of times and temperatures comprising at least a first temperature maintained for a first period of time and a second temperature maintained for a second period of time, with said second temperature being higher than said first temperature and said cycling comprising at least two repetitions of said sequence of times and temperatures.

It is to be understood that both the foregoing general description and the following description of various embodiments are exemplary and explanatory only and are not restrictive.

DRAWINGS

The accompanying drawings, which are incorporated in and constitute a part of this specification, illustrate several exemplary embodiments. In the drawings, FIG. 1 is a top perspective view of an exemplary embodiment of a thermal cycling device according to the present teachings;

DETAILED DESCRIPTION

Figure 1:
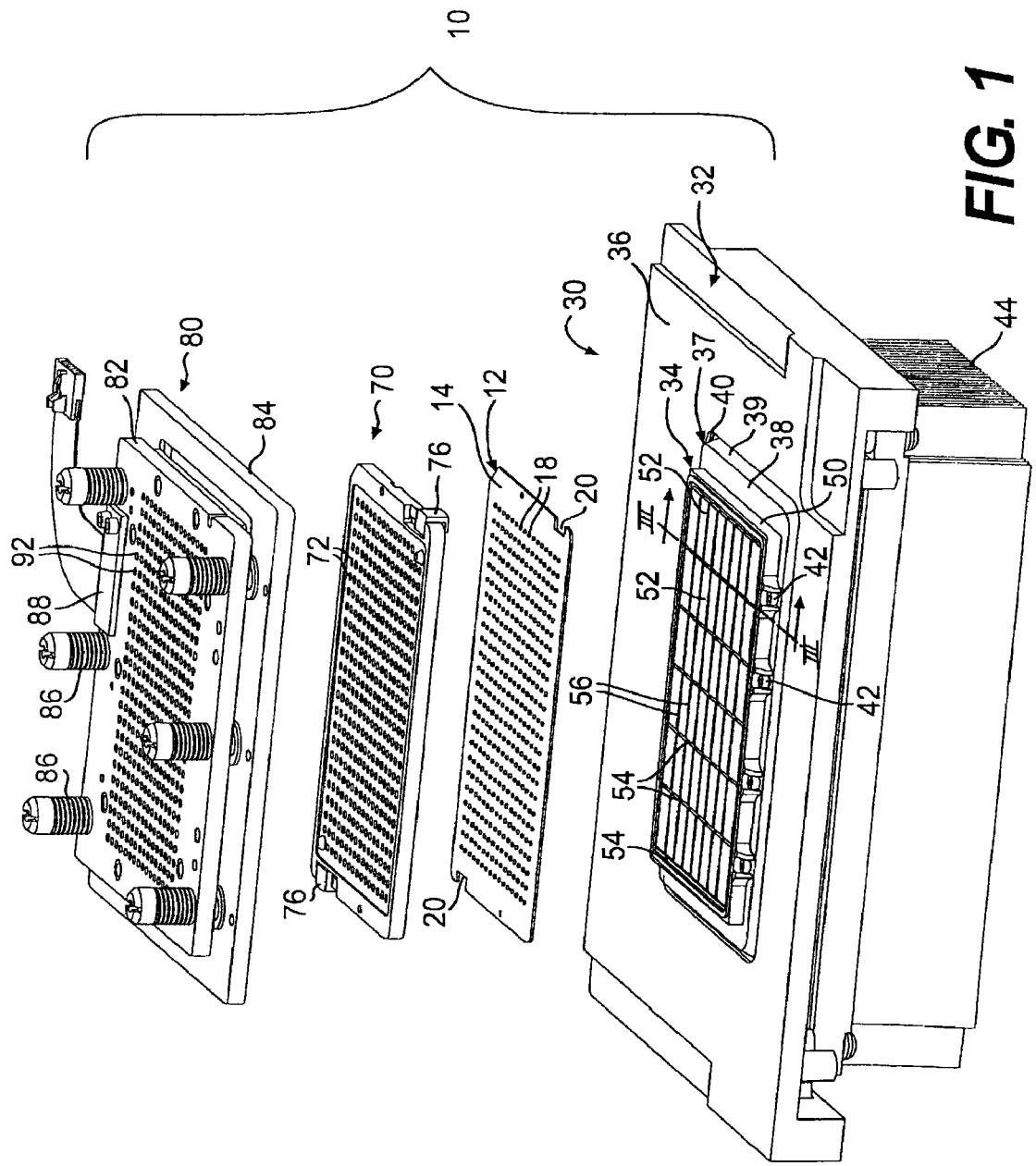
Figure 2:
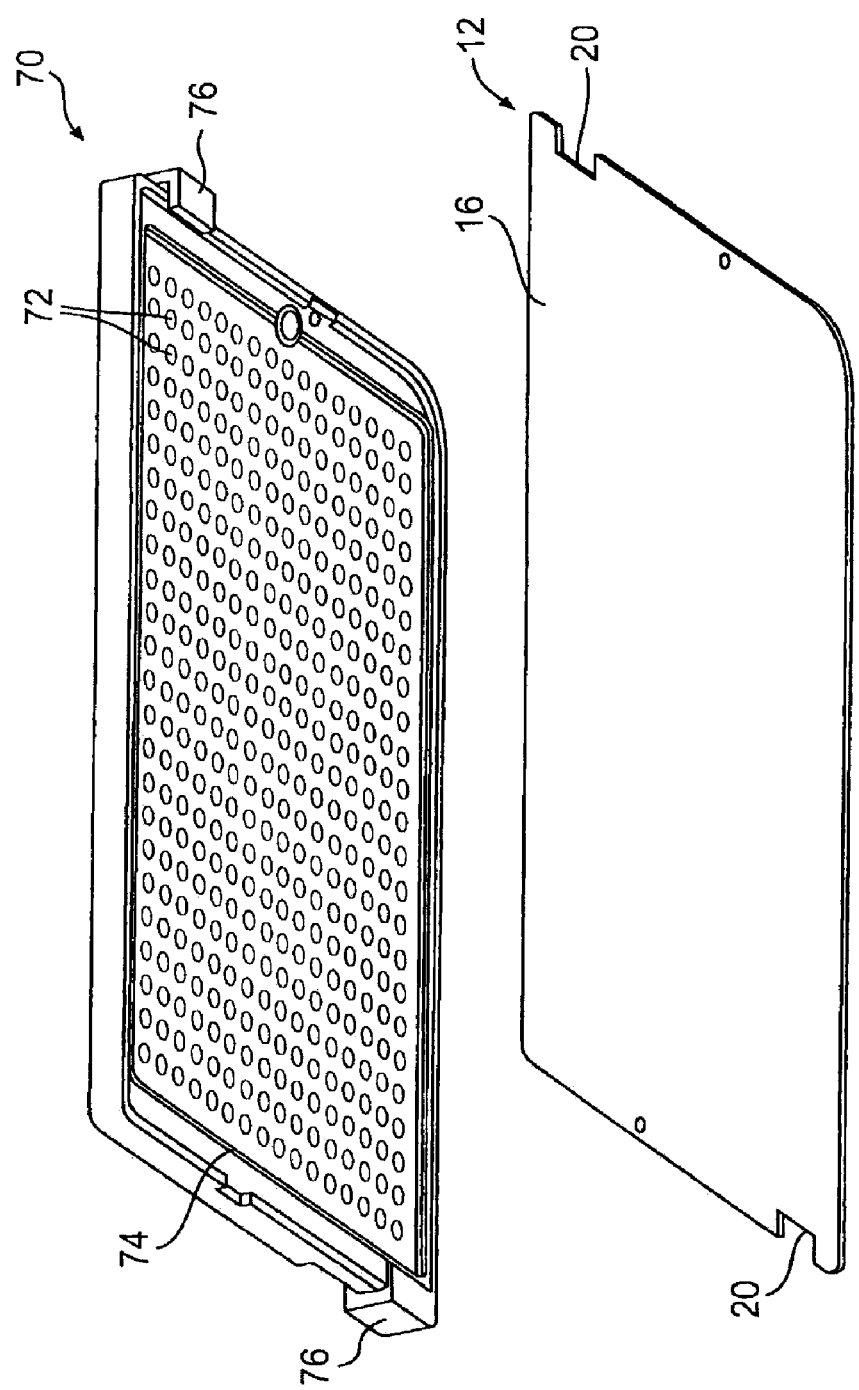
FIG. 2 is bottom perspective view of a microcard and microcard carrier of the thermal cycling device shown in FIG. 1.

Reference will now be made to various exemplary embodiments, examples of which are illustrated in the accompanying drawings. Wherever possible, the same reference numbers are used in the drawings and the description to refer to the same or like parts.

In accordance with various embodiments, a thermal cycling device is provided. In various aspects, the thermal cycling device may perform nucleic acid amplification on a plurality of biological samples positioned in a microcard. In various embodiments, the thermal cycling device includes a sample block. In various embodiments, the thermal cycling device may also include a microcard carrier and a cover.

Various embodiments are directed toward a sample block apparatus comprising a sample block, a vacuum source, and a temperature control system.

Although terms like "horizontal," "vertical," "upward," and "downward" may be used in describing various aspects of the present teachings, it should be understood that such terms are for purposes of more easily describing the teachings, and do not limit the scope of the teachings.

In various embodiments, such as illustrated in FIGS. 1-4, the thermal cycling device 10 configured for use with a microcard 12 includes a sample block apparatus 30, a microcard carrier 70, and a cover 80. The thermal cycling device may be configured to perform nucleic acid amplification on the samples of biological material. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In various embodiments, the thermal cycling device performs real-time detection of the nucleic acid amplification of the samples in the microcard during thermal cycling. Real-time optical detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification. In the embodiment shown in FIGS. 1-4, an optical detection system (not shown) is positioned above the microcard 12.

The thermal cycling device 10 shown in FIGS. 1-4 is particularly suited for use with a microcard. The microcard may be, in various embodiments, any type of two-dimensional array of sample loci held within a continuous or non-perforated substrate. This substrate may be flexible or rigid. The substrate or microcard may include any number of sample chambers for containing samples of the biological material. The most typical number of sample chambers is 60, 96, 384, or 1536, however, the microcard may include any other number of sample chambers from one to at least several thousand. FIG. 1 shows an example of a microcard sample tray having 384 wells. Several non-limiting examples of some sample well trays of the microcard type suitable for use in the present invention are described in WO 02/01180 to Bedingham et al., the complete disclosure of which is hereby incorporated by reference for any purpose, WO 01/28684 to Frye et al., the complete disclosure of which is hereby incorporated by reference for any purpose, and WO97/36681 to Woudenberg et al., the complete disclosure of which is hereby incorporated by reference for any purpose. Any number of other types of microcards are also contemplated for use herein.

As embodied herein and shown in FIGS. 1-4, microcard 12 is rectangular in shape. It should be understood that the microcard may be any other suitable shape. The microcard 12 has a top surface 14 and a bottom surface 16. The microcard may be made out of one or several pieces. In the example shown in FIGS. 1-4, the sample well tray includes 384 sample chambers 18 positioned in a well-known 16.times.24 array. The sample chambers may be loaded with biological materials in any of a variety of known manners (e.g., micropipetting). The volume of the sample chambers may vary depending on the number of sample chambers, and the specific application.

In the embodiment shown in FIG. 1, the microcard may include a pair of notches 20 for engaging with a microcard carrier in a manner that will be described below. It is contemplated that the microcard may be provided without such notches however.

In accordance with various embodiments, the thermal cycling device includes a sample block apparatus configured to receive the microcard thereon. As described herein and shown in FIGS. 1-4, the sample block apparatus is generally designated by the reference number 30. It is to be understood that the sample block apparatus shown in FIG. 1-4 is by way of example only, and the present teachings are not limited to the sample block apparatus shown in FIGS. 1-4. In the embodiment shown in FIGS. 1-4, sample block apparatus (or sample block) 30 comprises a sample block base 32 and sample block platform 34. Sample block platform is positioned on an inner region of the sample block base 32. A groove 40 on the top surface 36 of the sample block base 32 defines a recess in which the sample block platform 34 may be positioned.

Sample block platform 34 comprises a raised upper region with a top surface 52, and a support 37. The support 37 includes a flat upper surface 38 and angled support member 39. In the embodiment shown, the sample block platform may be removably attached to the sample block base 32 via a fastening member 42. In the example shown, the fastening member 42 is a threaded fastener. Any other type of fastening member may also be suitable. In other embodiments, the sample block platform may be integral with the sample block base 32.

The sample block base 32 and sample block platform 34 may be made out of any suitable material, such as aluminum, gold-plated silver, or a thermally-conductive polymer/plastic. The material can be heat conductive so that the sample block may assist in thermal cycling. The sample block base 32 may be attached to any known type of heat sink. In the embodiment shown in FIGS. 1-4, the heat sink is a finned heat sink 44. The sample block typically includes at least one heating element. In various embodiments, the at least one heating element includes a peltier heater. Other types of heating elements may be used instead of, or in combination with, the peltier heater. A convection unit such as a fan may also be positioned adjacent the heat sink 44.

The sample block may be operatively connected to a temperature control system programmed to raise and lower the temperature of the sample block according to a user-defined profile. Several non-limiting examples of suitable temperature control systems for raising and lowering the temperature of the sample block are described in U.S. Pat. No. 5,656,493 to Mullis et al. and U.S. Pat. No. 5,475,610 to Atwood et al., the disclosures of which are both hereby incorporated by reference for any purpose. For example, in various embodiments, a user supplies data defining time and temperature parameters of the desired PCR protocol to a control computer that causes a central processing unit (CPU) of the temperature control system to control thermal cycling of the sample block. In a typical thermal cycler of the present teachings, the temperature control system may be configured for cycling the sample block through a sequence of times and temperatures comprising at least a first temperature maintained for a first period of time and a second temperature maintained for a second period of time, with the second temperature being higher than the first temperature, and the cycling comprising at least two repetitions of said sequence of time and temperatures.

In accordance with various embodiments, the sample block comprises an upper surface configured for resting a microcard thereon during thermal cycling of the microcard. The upper surface includes surface irregularities for defining a space between selected regions of the upper surface and a microcard positioned thereon during thermal cycling. In various embodiments, the surface irregularities comprise channels or recesses. As embodied herein, and shown in FIGS. 1-4, the sample block platform 34 may be a rectangular block of material with a side surface 50 and an upper surface 52. As shown in FIGS. 1-5, the upper surface includes a plurality of channels (or recesses or voids) positioned in a perpendicularly intersecting manner. For sake of simplifying the description of the channels (or recesses or voids) in the specification, the channels shown in FIGS. 1-4 will be referred to as lateral channels 54 and longitudinal channels 56. As shown in FIG. 1, the lateral channels 54 have a shorter length than the longitudinal channels 56. In the embodiment shown in FIG. 1, the upper surface includes seven lateral channels 54 and nine longitudinal channels 56. Any other number of lateral and longitudinal channels may be used instead.

Although FIGS. 1-4 show the channels being positioned in a perpendicularly intersecting manner, it should be understood that the channels may be in any other geometric shape. The perpendicularly intersecting pattern is shown for purposes of example only. The positioning on the channels may be a function of the microcard features. In various embodiments, it may be generally desirable to position the channels so that the channels are not positioned immediately below the sample chambers 18. Instead, it may be desirable to have the top flat surface 52 contacting the bottom surface 16 of the microcard 12 in the area immediately below the sample chambers 18. One reason for this is that it may be desirable that the bottom surface of the microcard directly below the sample chamber be directly in contact with the upper surface 52 of the sample block platform, in order to minimize temperature differences between adjacent samples.

Figure 3:
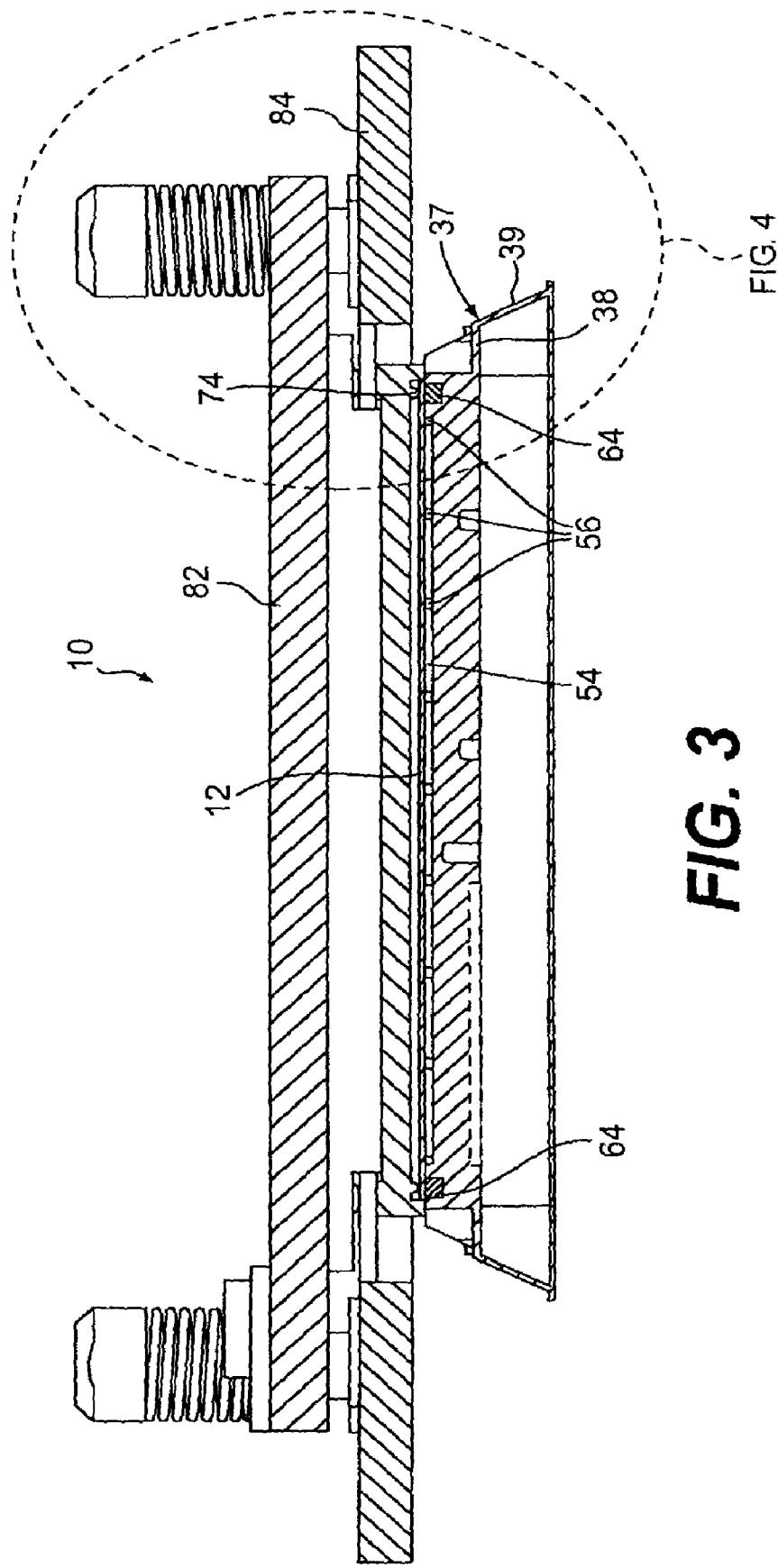
FIG. 3 is a side cross-sectional view of the thermal cycling device of FIG. 1 along line III-III of FIG. 1, in an assembled state.
Figure 4:
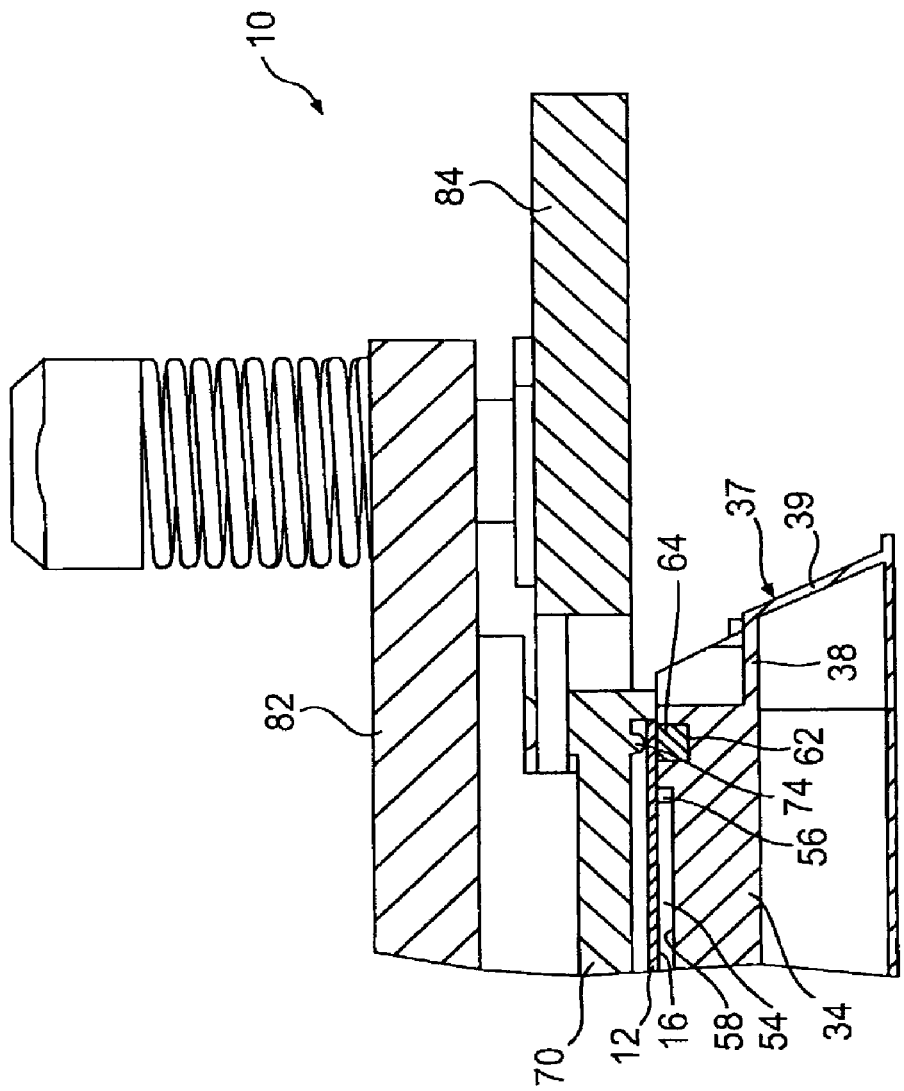
FIG. 4 is a close up cross-sectional view of a portion of the thermal cycling device of FIG. 3.

FIGS. 3 and 4 show the thermal cycling device of FIG. 1 in the assembled state. The cross-section shown in FIGS. 3 and 4 is taken along a lateral channel 54 as indicated by the line III-III in FIG. 1. FIGS. 3 and 4 show the space created by lateral channel 54 under bottom surface 16 of microcard 12, when the microcard 12 is placed on the upper surface 52 of the sample block platform. FIG. 4 also shows the width and depth of longitudinal channel 56 that intersects with the lateral channel 54 along which the cross-section is taken. When the microcard is placed on the upper surface 52 of the sample block platform, the channels define spaces in which a vacuum may be imparted as described below. In accordance with the embodiment shown in FIGS. 1-4, the spaces are in fluid communication with one another so that a vacuum may be drawn in the spaces.

The channels (or recesses or voids) may be formed in the upper surface 52 by any known manner. The width and depth of the channels may be varied from that shown in FIGS. 3 and 4. In FIG. 4, reference number 58 indicates the lower surface of lateral channel 54. When the microcard 12 is inserted into the thermal cycling device, the bottom surface 16 of the microcard rests flush against the upper surface 52 of the sample block platform. Because there remains a large amount of surface area of the microcard that is in contact with the upper surface 52 of the sample block, the sample block may effectively perform its function of transferring heat to and away from the microcard before, during, and/or after thermal cycling.

In various embodiments, the sample block apparatus further includes a vacuum device in fluid communication with the sample block platform for drawing gas, such as air, out of the spaces defined by the channels in the sample block platform. The vacuum device is configured for substantially maintaining a vacuum between the sample block platform and microcard so that a downward force is imparted on the microcard to urge the microcard toward the sample block platform. The vacuum device may be connected to the sample block via a vacuum port positioned on or in the sample block platform. In the embodiment of FIGS. 1-4, the vacuum port is positioned along the rear edge of the sample platform, and is therefore out of view in FIGS. 1-4. The vacuum port may be an aperture with a passage in direct communication with channels 54 and 56. By attaching a vacuum device to the sample block platform, a vacuum may be drawn in the channels, thereby pulling downward on the microcard. The resulting downward force may be sufficient to retain the microcard on the sample block platform. The downward force from the vacuum in the spaces beneath the microcard can assist in maintaining the microcard firmly pressed against the upper surface 52 of the sample block platform, thereby promoting substantial temperature uniformity between the sample chambers 18, if desired.

Moreover, in real-time detection apparatuses, it may be desirable to minimize the amount of structure located between the microcard and the optical detection system. In various embodiments, the provision of the vacuum in the spaces under the microcard eliminates the need for an apparatus such as a plate positioned above the microcard that presses against the upper surface in the spaces between the sample chambers. By eliminating the need for such a pressing plate, it may be possible to utilize a greater portion of the upper surface for sample chambers. If a pressing plate is not used, space does not need to be reserved for pressing on the upper surface of the microcard. It may be desirable that there is a sufficient initial downward force on the microcard so that an initial vacuum can be drawn.

It should be understood that the channels 54 and 56 shown in FIGS. 1-4 are not the only type of surface irregularity suitable with the present invention. In other embodiments of the present invention, the upper surface 52 of the sample block platform may include a rough surface instead of the channels shown in FIGS. 1-4. The rough surface is preferably of sufficient roughness so that the spaces created by the valleys of the irregularities can have a substantial vacuum imparted on them. The depth of the surface irregularities may depend on the rigidity of the microcard. For example, if the microcard is very stiff it is possible to draw a sufficient vacuum with only very small irregularities. Other types of surface irregularities can also be used with the present invention.

In various embodiments, the sample block platform may further include a groove positioned around the outer periphery of the sample block platform channels. In the exemplary embodiment shown in FIGS. 1-4, a groove 62 is formed around the outer periphery of the upper surface 42 of the sample block platform, in an area outside of the channels 54 and 56. The groove surrounds the recessed area of the upper surface 42 of the sample block platform. In the embodiment shown in FIGS. 3 and 4, the groove is rectangular in shape, however, any other suitable shape is also acceptable. In the embodiment shown in FIG. 4, a gasket 64 is inserted in the groove 62 to surround the recessed area. The gasket may be configured to engage a bottom surface 16 of the microcard carrier 12. The gasket may be any type or shape of gasket capable of facilitating a vacuum seal between the microcard 12 and sample block platform 34. In various embodiments, the gasket is suitable for use in a thermal cycling device. It should be understood that a complete vacuum may not be necessary. A substantial vacuum may be sufficient to initiate a downward urging force from the microcard onto the gasket and upper surface 52 of the sample block platform.

In accordance with various embodiments, the thermal cycling device may also include a microcard carrier. As described herein and shown in FIGS. 1-4, the microcard carrier 70 is a rectangular shaped object with a length and width slightly larger than the microcard. In the present invention, the microcard carrier serves the purpose of pressing downwardly around the outside periphery of the top surface 14 of the microcard 12. In the embodiment shown in FIGS. 1-4, the microcard carrier includes a downwardly projecting rib 74 on a lower surface of the microcard. The microcard carrier is optional, but it can be helpful for use with flexible microcards.

In the embodiment shown in FIGS. 1-4, the microcard carrier 70 includes a plurality of optical openings 72 for permitting light to pass through between optical detection system and the sample chambers during detection (e.g., real-time detection) of the biological samples in the sample chambers 18. In the embodiment shown in FIGS. 1-4, the plurality of openings 72 are aligned with the sample chambers 18. The downwardly projecting rib 74 of the microcard carrier 70 may be positioned around the outer periphery of the optical openings 72. In the embodiment shown, the rib 74 presses downwardly on an outer periphery of the microcard 12. The engagement of the rib with the microcard assists in sealing the microcard 12 against gasket 64 to form an initial seal. In various embodiments, the microcard carrier can be removed after the vacuum is drawn below the microcard.

The microcard carrier 70 may also include a pair of guide members 76 for engagement with the notches 20 that may be provided in the microcard 12. The guide members 76 and notches 20 may assist in preventing horizontal movement between the microcard and the microcard carrier. In various embodiments, the microcard and microcard carrier may snap-fit together. It should be understood that the guide members and notches are optional.

In various embodiments, the thermal cycling device may also comprise a cover. FIG. 1 shows a cover 80 which may be heated by heating element 88. Alternately, in various embodiments, the cover might not be heated. The heated cover 80 of FIGS. 1-4 includes, among other things, a top plate 82, bottom plate 84, a plurality of spring elements 86, and heating element 88. The top plate 82 includes a plurality of optical openings 92 for permitting light to pass through between the optical detection system and the sample chambers during detection (e.g., real-time detection) of the biological samples in the sample chambers 18. The cover may assist in evenly distributing the force imparted on the microcard by microcard carrier 70. It should be understood that the cover is optional. In the embodiment shown in FIGS. 1-4, the cover 80 may assist in providing the downward force on microcard 12. In one embodiment, the bottom plate 84 may be pushed downward, thereby pulling down on spring elements 86, thereby pushing top plate 82 in the downward direction. Top plate 82 may then press downward on microcard carrier 70, which then presses downward on microcard 12 via the downwardly projecting rib 74.

In various embodiments, a seal can be maintained between microcard 12 and sample block platform 34 without a microcard carrier and cover. This can be true, for example, when the microcard carrier has a high rigidity. A rigid microcard may tend to be more resistant to warping than a flexible microcard, and therefore may be able to maintain a seal with the gasket without any external force (such as a microcard carrier) pressing downward on it. If the microcard is very flexible and prone to warping, it may be helpful to provide some type of device for pressing downward on the microcard in the area adjacent the gasket.

An operation of the thermal cycling device for the embodiment of FIGS. 1-4 is described below. First, the microcard carrier 70 and a microcard 12 with samples of biological material (e.g., DNA) are positioned on the flat upper surface 52 of the sample block platform. The microcard carrier is positioned such that downwardly projecting rib 74 engages the top portion of microcard 12. The cover 80 may then be placed over the top of the microcard and microcard cover. In the embodiment shown in FIGS. 1-4, the cover 80 may assist in pressing downward on the microcard carrier 70 and microcard 12. The outer periphery of microcard 12 is thus firmly pressed against the top surface of gasket 64.

Next, a vacuum source is attached to a vacuum port on the side of the sample block so that any air positioned in the spaces defined by channels 54 and 56 and a bottom surface 16 of the microcard is evacuated. When the space is at a substantial vacuum, the microcard will be pulled downward by the vacuum so that the microcard is firmly pressed against the top flat surface 52 of the sample block platform 34. In this manner, no large forces are needed on the top central portion of the microcard and substantial temperature uniformity across the sample chambers may be achieved, if desired. Thermal cycling of the apparatus may now be performed, with or without real-time detection by the optical detection system. During thermal cycling, the temperature control system of the thermal cycling device is operatively connected to the sample block to cause the temperature of the sample block to raise and lower according to a pre-programmed protocol. In one embodiment, the sample block (and microcard) are thermally cycled through a sequence of times and temperatures comprising at least a first temperature maintained for a first period of time and a second temperature maintained for a second period of time. The second temperature is higher than the first temperature. The thermal cycling includes at least two repetitions of the sequence of time and temperatures. After the thermal cycling is completed, the microcard and microcard carrier may then be removed.

Figure 5:
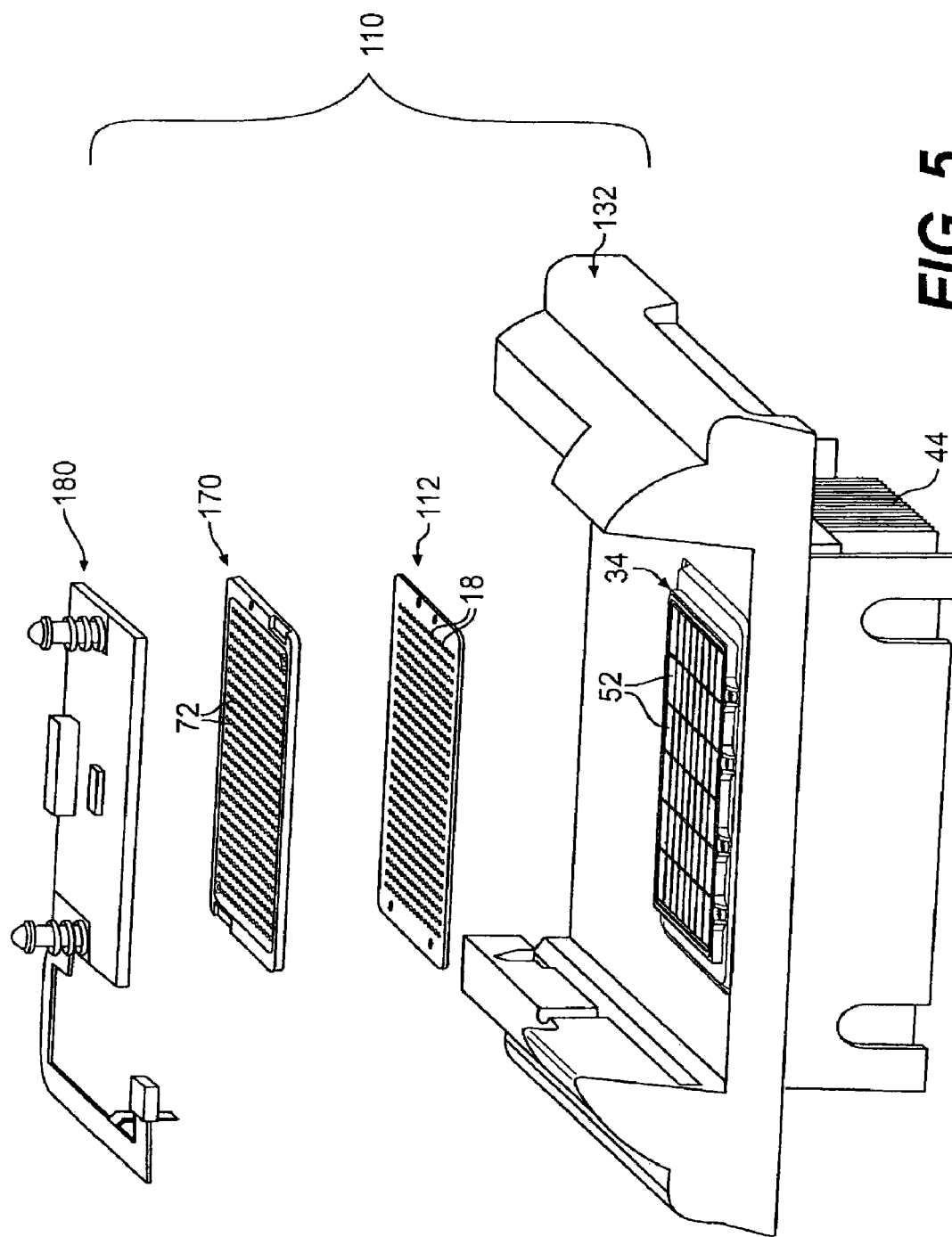
FIG. 5 is a top perspective view of a thermal cycling device according to another embodiment of the present teachings.

Further various embodiments of the thermal cycling device contemplate structure such as shown in FIG. 5. The thermal cycling device of FIG. 5 is generally designated by the reference number 110. To the extent that the following structure is identical to the structure described for FIGS. 1-4, a description will not be repeated. FIG. 5 shows a thermal cycling device comprising a sample block, microcard, microcard carrier, and heated cover. The microcard 112 is essentially identical to microcard 12 of FIGS. 1-4, however, it lacks notches for engagement with a microcard carrier. The microcard carrier 170 is similar to the microcard carrier 70 of FIGS. 1-4. Heated cover 180 may be slightly different from heated cover 80 of FIGS. 1-4. The sample block platform, however, may be identical to the sample block platform 34 described above for FIGS. 1-4, and is therefore also labeled with reference number 34. The sample block platform 34 has the same channels on the upper flat surface as described for FIGS. 1-4, and operates in an identical manner. Unlike FIGS. 1-4, FIG. 5 shows the outer walls of the sample block base 132, as is known in the art.

The operation of the thermal cycling device for the embodiment of FIG. 5 corresponds to the operation described above for the embodiment shown in FIGS. 1-4, therefore a description of the operation will not be repeated. Moreover, the same reference numbers are used to refer to the same or like parts as shown in the embodiment of FIGS. 1 and 2A-2C. It should be understood that, similar to the FIGS. 1-4 embodiment, cover 180 and microcard carrier 170 are optional.

Figure 6:
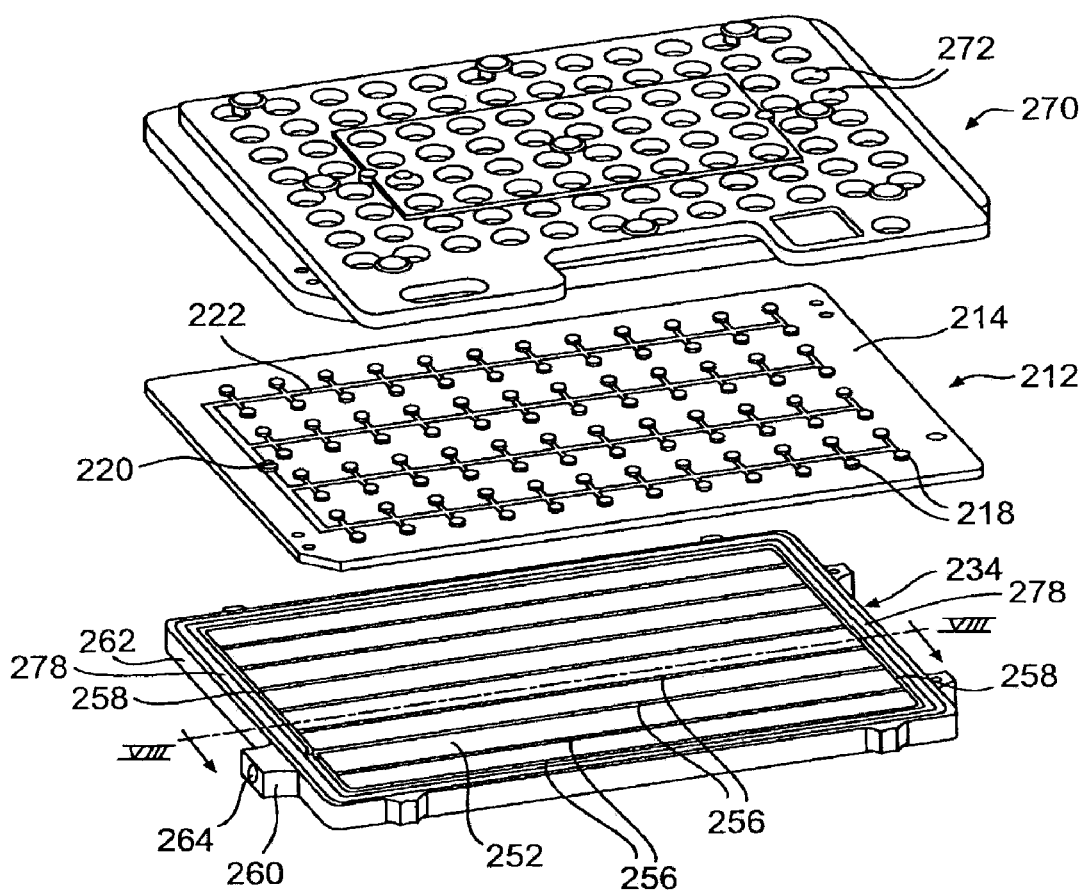
FIG. 6 is a top perspective view of a sample block platform, microcard, and microcard carrier according to another embodiment of the present teachings.
Figure 7:
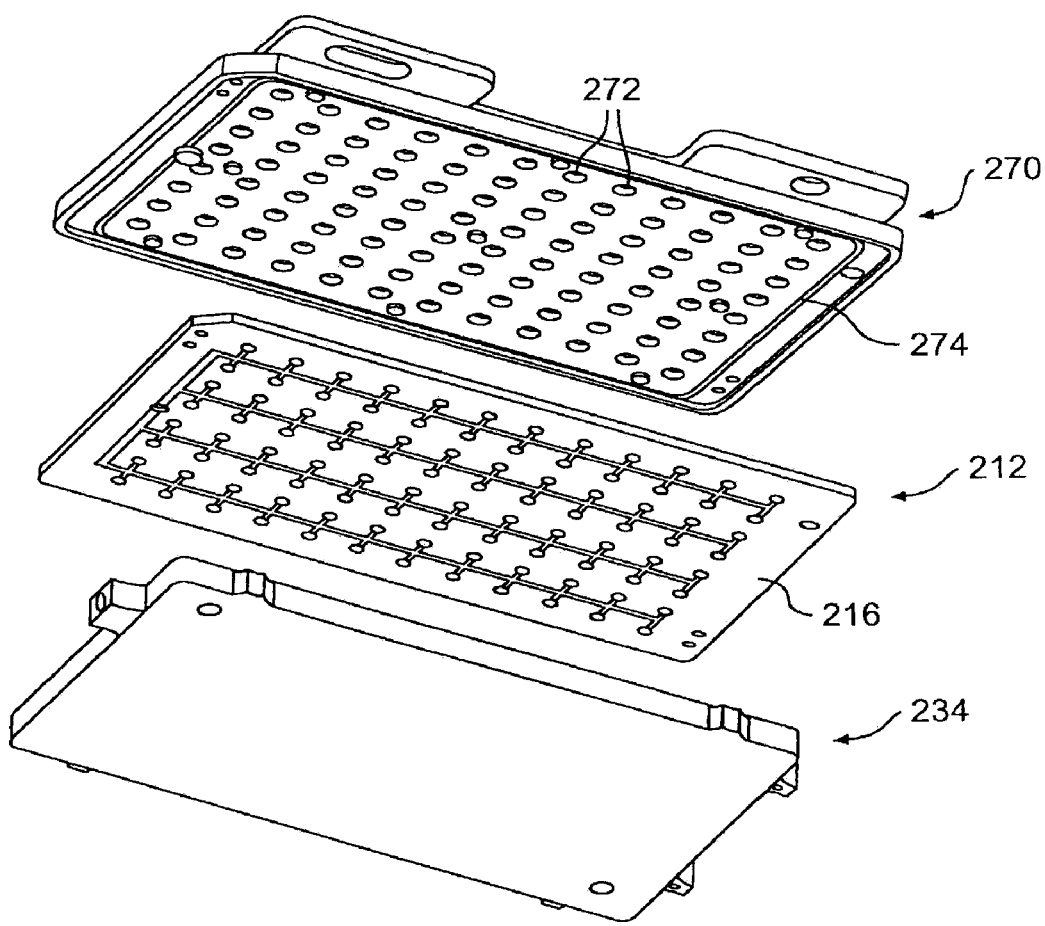
FIG. 7 is a bottom perspective view of the sample block platform, microcard, and microcard carrier of FIG. 6.
Figure 8:
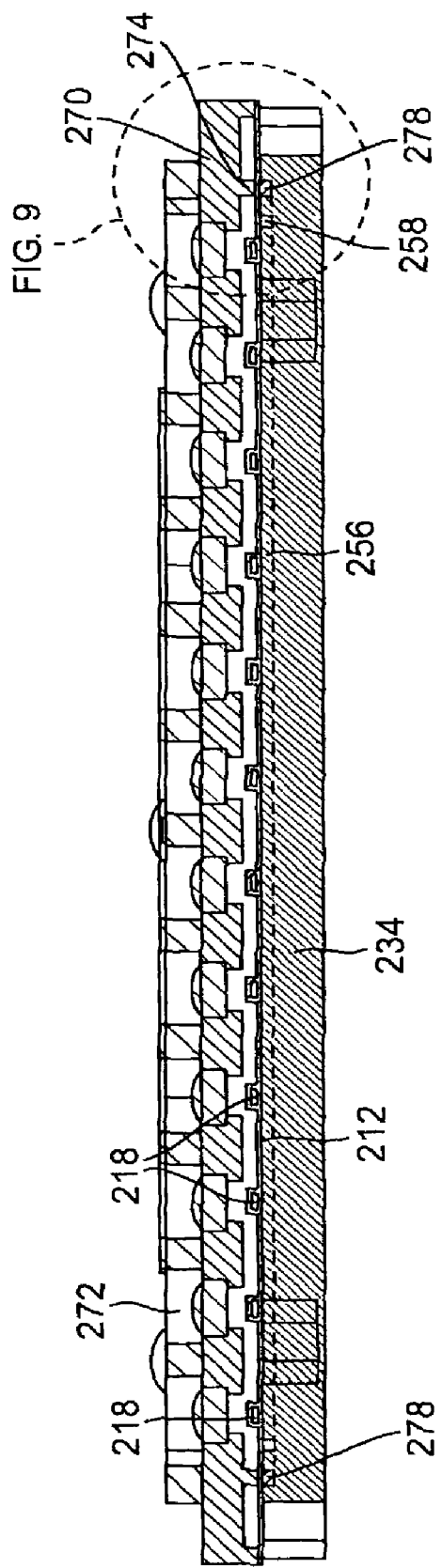
FIG. 8 is a cross-sectional view of the sample block platform, microcard, and microcard carrier along line VIII-VIII of FIG. 6, in an assembled state.
Figure 9:
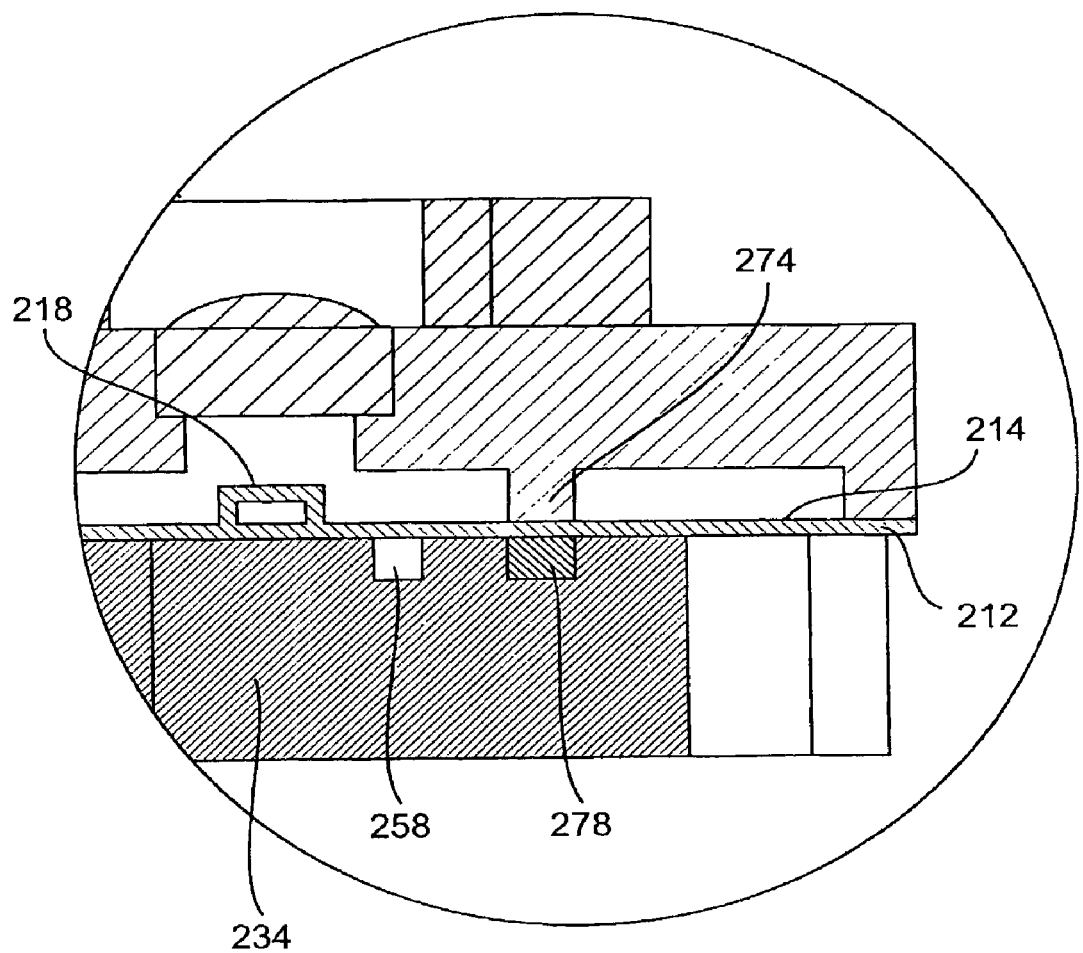
FIG. 9 is a close up cross-sectional view of a portion of the sample block platform, microcard, and microcard carrier of FIG. 8.

FIGS. 6-8 show still further embodiments of a sample block platform, microcard, and microcard carrier according to the present invention. In particular, FIGS. 6-8 show a microcard having 96 chambers. An example of a microcard of this type is described in WO 01/286684 to Frye et al., incorporated herein above. Microcard 212 includes a top surface 214 and bottom surface 216. The microcard includes 96 chambers 218 that are fluidly connected to one another as described in greater detail in WO 01/286684. In the embodiment shown in FIGS. 6-8, the microcard can be filled via sample inlet port 220 and longitudinal delivery passageways 222, using, for example, a vacuum.

The embodiment of FIGS. 6-8 includes a sample block platform similar to that shown in FIGS. 1-4 and FIG. 5, with several exceptions. The sample block platform 234 shown in FIGS. 6-8 includes a plurality of longitudinal channels 256 in addition to two lateral channels 258 connected to the ends of the longitudinal channels. In various embodiments, each of the channels is fluidly connected to one another so that a vacuum may be drawn in the space below the microcard when the microcard is placed on the upper surface 252 of the sample block platform. When the microcard is placed on top of the sample block platform, a space is defined by the channels 256 and 258 and the bottom surface 216 of the microcard.

As shown in FIG. 6, the sample block platform may include a vacuum port 260 positioned on the side 262 of the sample block platform. The vacuum port corresponds to the vacuum port that could be used in the FIGS. 1-4 and FIG. 5 embodiments. The vacuum port 260 has an internal passageway 264 that is fluidly connected to the channels 256 and 258 of the sample block platform. By connecting a vacuum device to the vacuum port, a substantial vacuum can be drawn in a manner described below.

The thermal cycling device of FIGS. 6-8 may further include a microcard carrier 270. As shown in FIGS. 6-8, the microcard carrier includes a number of optical openings 272 that permit radiation to pass through the carrier. Lenses may also be positioned in the optical openings, if desired. The microcard carrier may also include a downwardly projecting rib 274 for engagement with top surface 214 of microcard 212.

FIG. 8 illustrates a cross-sectional view of the apparatus of FIGS. 6-7, taken along line VIII-VIII in FIG. 6. The channels 256 in this embodiment are not positioned immediately below the sample chambers 218. FIG. 8 shows a cross-section along a line passing through the sample chambers, therefore, the channel 256 is only shown as a dashed line. As seen in FIG. 8, the spaces above the sample chambers 218 are surrounded by air, and are not in direct contact with the microcard carrier 270. The microcard may remain in firm contact with the upper surface 272 of the sample block platform 234 due to the operation of the vacuum device.

As is clear from the above descriptions of various embodiments, the present teachings include a method of maintaining a microcard on a sample block of a thermal cycling device. The method can include the steps of providing a sample block with a plurality of channels on an upper surface thereof. The method may further include the step of providing a space above the upper surface of the sample block for a microcard containing at least one sample of biological material so that a bottom surface of the microcard may contact the upper surface of the sample block. A vacuum may then be imparted on the spaces defined by the channels on the upper surface of the sample block and the bottom surface of the microcard positioned adjacent the upper surface of the sample block, the vacuum creating a force to urge the adjacent microcard against the upper surface of the sample block. The microcard may then be thermally cycled through a sequence of times and temperatures comprising at least a first temperature maintained for a first period of time and a second temperature maintained for a second period of time, with said second temperature being higher than said first temperature. Simultaneously with the step of thermally cycling the microcard, the optical characteristics of the at least one sample of biological material or of one or more detectable markers associated therewith may be detected. In accordance with various embodiments, a gasket may be provided on an outer peripheral surface of the sample block, the gasket contacting and forming a seal with the bottom surface of the microcard during thermal cycling of the microcard.

It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. A thermal cycling device for thermally cycling samples of biological material, the thermal cycling device comprising:
   a microcard having a top surface and a bottom surface, the microcard comprising a plurality of chambers each containing samples of biological material and at least one primer;
   a sample block having an upper surface and a plurality of channels formed along the upper surface, the upper surface of the sample block being in contact with and supporting the bottom surface of the microcard such that the bottom surface of the microcard overlays the plurality of channels to form a sealed volume;
   a temperature control system operably coupled to the sample block, the temperature control system cycling the sample block through a polymerase chain reaction temperature cycle; and
   a vacuum device in fluid communication with the plurality of channels formed in the sample block, said vacuum device exerting and maintaining a vacuum within the sealed volume to urge the microcard toward the sample block to maximize thermal contact between the microcard and the sample block and permit generally uniform and consistent temperature cycling of the microcard.

2. The thermal cycling device of claim 1 wherein the plurality of channels comprise a plurality of perpendicularly intersecting grooves.

3. The thermal cycling device of claim 1 wherein the plurality of channels comprise a plurality of substantially parallel grooves.

4. The thermal cycling device of claim 1, further comprising:
   a gasket positioned around an outer periphery of the plurality of channels in the sample block, the gasket configured to engage the bottom surface of the microcard when the microcard is positioned on the sample block.

5. The thermal cycling device of claim 4, further comprising:
   an outer groove disposed about the outer periphery of the channels in the sample block, the gasket being positioned in the outer groove.

6. The thermal cycling device of claim 1, further comprising:
   a microcard carrier positioned above the microcard when the microcard is positioned on the sample block.

7. The thermal cycling device of claim 6 wherein the microcard carrier comprises:
   at least one downwardly projecting rib engaging an outer periphery of the top surface of the microcard, the rib pressing downward on the outer periphery of the top surface of the microcard to assist in maintaining a vacuum within the sealed volume.

8. The thermal cycling device of claim 7 wherein the microcard carrier comprises:
   at least one opening generally aligned with at least one of the plurality of chambers in the microcard.

9. The thermal cycling device of claim 7, further comprising:
   a cover engaging and downwardly urging the microcard carrier.

10. The thermal cycling device of claim 1, further comprising:
    a microcard carrier in contact with the microcard when the microcard is positioned on the sample block, the microcard carrier being configured to press on the microcard.

11. The thermal cycling device of claim 10, further comprising:
    a cover configured to contact the microcard carrier, the cover being configured to press on the microcard carrier.

* * * * *